United States Patent [19]

Devillez

[11] Patent Number: 5,641,507

[45] Date of Patent: Jun. 24, 1997

[54] DELIVERY SYSTEM FOR DERMATOLOGICAL AND COSMETIC INGREDIENTS

[76] Inventor: Richard L. Devillez, Rte. 1, Box 92, D-1, Hondo, Tex. 78861

[21] Appl. No.: 548,419

[22] Filed: Oct. 26, 1995

Related U.S. Application Data

[63] Continuation of Ser. No. 163,676, Dec. 6, 1993, abandoned.

[51] Int. Cl.$^6$ ...................................................... A61F 13/00
[52] U.S. Cl. ........................ 424/443; 424/401; 424/448
[58] Field of Search .................................. 424/448, 449, 424/401, 443

[56] References Cited

U.S. PATENT DOCUMENTS

| | | | |
|---|---|---|---|
| 3,797,494 | 3/1974 | Zafffaroni | 424/434 |
| 4,031,894 | 6/1977 | Urquhart | 424/448 |
| 4,176,664 | 12/1979 | Kalish | 604/307 |
| 4,379,454 | 4/1983 | Campbell | 424/448 |
| 4,762,124 | 8/1988 | Kerch | 604/307 |
| 5,028,431 | 7/1991 | Franz et al. | 424/449 |
| 5,141,750 | 8/1992 | Lee et al. | 424/448 |

*Primary Examiner*—D. Gabrielle Phelan
*Attorney, Agent, or Firm*—Gunn, Lee & Miller, P.C.

[57] ABSTRACT

Various embodiments of a delivery system for the effective and efficient administration of low viscosity cosmetic and dermatological ingredients without the use of plasters or repetitive applications that are currently necessary. The claimed embodiments eliminate migration of the low viscosity application liquid to areas where treatment is not required and/or sensitive areas of the patient's body which could be adversely affected if contacted by the application liquid.

8 Claims, 4 Drawing Sheets

DELIVERY SYSTEM FOR DERMATOLOGICAL AND COSMETIC INGREDIENTS

This is a Continuation of application Ser. No. 08/163,676, filed on Dec. 6, 1993, now abandoned

BACKGROUND OF THE INVENTION

1. Field of the Invention

Applicant's invention relates to a delivery system for efficient and effective administration of dermatological and cosmetic ingredients. Specifically, Applicant's invention addresses the application of low viscosity liquids for an extended period of time without migration of the liquid to areas other than the treatment site. Applicant's invention may also be used in conjunction with liquids which become low viscosity liquids after volatile ingredients evaporate.

2. Background of the Invention

A variety of low viscosity cosmetic and dermatological ingredients could be applied more effectively, efficiently, and safely if a simple delivery system was available for the continuous and controlled application of the liquid to a specific skin area without migration occurring. As used herein, a low viscosity liquid is a liquid that has a viscosity less than 1000 cPs. Applicant's invention may also be used in conjunction with a high viscosity liquid that becomes a low viscosity liquid after evaporation of volatile ingredients. Some examples of low viscosity liquids include water based solutions, alcohol solutions and hydro-alcohol solutions. Examples of high viscosity liquids that become low viscosity liquids after evaporation include emulsified products such as creams or gels that contain low viscosity non-volatiles.

To prevent the low viscosity liquid from migrating to areas that do not require treatment and/or are sensitive areas such as the eyes or scrotum that may be adversely affected by the application liquid, health care professionals currently either: (1) apply the application liquid repeatedly, which necessitates the health care professional devote constant attention to the treatment; or (2) apply the application liquid as a plaster or as a solution in flexible collodion which dries to form a solid film.

As an example, salicylic acid dissolved in an hydro-alcoholic solution is a low viscosity liquid that is commonly used in the removal of warts, corns, bunions, callouses, actinic keratoses and hard hyperkeratotic skin on the feet by medical professionals. Due to the irritation potential and migration qualities of salicylic acid in solution, the Food and Drug Administration does not allow its sale over the counter. Rather, it is only available in plasters or solutions in a flexible collodion to the general public. Unfortunately, the plaster or flexible collodion treatment is much less effective than direct application because the plasters and collodion vehicles do not allow direct application nor delivery of sufficient quantities of the salicylic acid to the treatment site. Consequently, repetitive applications are required for effective treatment. Current state of the art treatments for wart removal utilizing a commercial corn remover which is a 30 mg, 12 mm disc containing 40% salicylic acid requires multiple treatments encompassing over 12 hours to remove the wart. Other cosmetic and therapeutic applications that face the same inefficient and ineffective application techniques include alpha-hydroxy acids, corticosteroids such as hydrocortisone and betamethasone, local anesthetics such as lidocaine and benzocaine, antibiotics, hydrogen peroxide and coal tar solutions. Consequently, a need exists for a delivery system for the efficient and effective continuous application of low viscosity dermatological or cosmetic ingredients which may be used by both the medical community and the public at large.

SUMMARY OF THE INVENTION

This invention finds great utility in conjunction with the application of low viscosity liquids, or liquids that become low viscosity after volatile ingredients evaporate, for the treatment of numerous cosmetic and therapeutic ailments. In accordance with this invention, a delivery system has been developed which incorporates a porous or fibrous reservoir that is either dimensionally stable (non-squeezable) or is contained in a dimensionally stable environment, a transfer pad and a mask if necessary.

Although not wanting to restrict himself to one theory, the applicant believes the release of the application liquid to the treatment site depends upon the reservoirs' capillary attraction to the application liquid versus the skin's capillary attraction to the liquid. It has been found that the skin in contact with the transfer pad will initially become wet with the application liquid. Yet once the skin is wet, further release of the application liquid from the transfer pad does not occur until the skin in direct contact with the transfer pad begins to dry. Applicant believes this occurs because the drying causes a shift in the equilibrium between the liquid in the reservoir and the drying skin, ie: the capillary attraction between the dry skin and the application liquid becomes greater than the capillary attraction between the reservoir and the application liquid. Once the skin in direct contact with the transfer pad has become wet, the skins' capillary attraction lessens to a point that the reservoir's capillary attraction becomes greater thus allowing the reservoir to immobilize the application liquid in the transfer pad. This immobilization prevents drainage from the transfer pad and thus migration to areas of the skin not in contact with the transfer pad. As the application liquid on the skin begins to absorb, the strength of the capillary attraction between the skin and the application liquid again becomes greater than the reservoirs' capillary attraction. Consequently, more liquid is released from the transfer pad and reservoir. This seesaw exchange between the skin and the reservoir continues until the reservoir has released most of the application liquid.

In a first embodiment of the applicant's invention, the low viscosity application liquid is loaded into a dimensionally stable porous reservoir. At least a portion of the reservoir is in direct contact with a transfer pad attached to the treatment site. In a modified version of this embodiment the porous reservoir is surrounded by a dimensionally stable shell which has an opening that allows a portion of the reservoir to directly contact the transfer pad. The transfer pad is either the same size as the treatment site or, if larger, the treatment site is framed by a mask that prevents the transfer pad from contacting the surrounding areas of the treatment site.

In a second embodiment of applicant's invention, the delivery system includes a connector strip between the reservoir and the transfer pad. This makeup enables the reservoir to be located at a remote site from the treatment site. The remote application system may be used when the treatment site is not conducive for attachment of the reservoir. For example, treatment of a wart on the heel of the foot. Again, the transfer pad may be the same size or larger than the treatment site. In some instances, the connector strip may act as the transfer pad if the treatment site is small. In this scenario, a hole is placed in the covering of the connector strip at the treatment site, allowing the connector strip to contact the treatment site directly.

A third embodiment of the invention includes a second reservoir. This embodiment allows for the irrigation of the treatment site with fresh solution from a reservoir containing the application liquid while unwanted fluid is continuously removed from the treatment site to a second reservoir. This embodiment could be used to continuously apply antibiotics, etc. to a burn area while simultaneously and continuously removing exudates, etc. from the area.

Further objects and advantages of the invention will be readily apparent to those skilled in the art from the following detailed description, taken in conjunction with the sheets of drawings.

DETAILED DESCRIPTION OF THE PREFERRED EMBODIMENT

The following detailed description is provided to aid those skilled in the art to practice the present invention. Even so, the following discussions and examples should not be deemed to unduly limit the present invention, since modifications may easily be made in the procedures herein taught by one of ordinary skill in the art, without departing from the spirit or scope or the present invention. In this regard, the present invention is only to be limited by the scope of the claims appended hereto and equivalents thereof.

Figure 1:
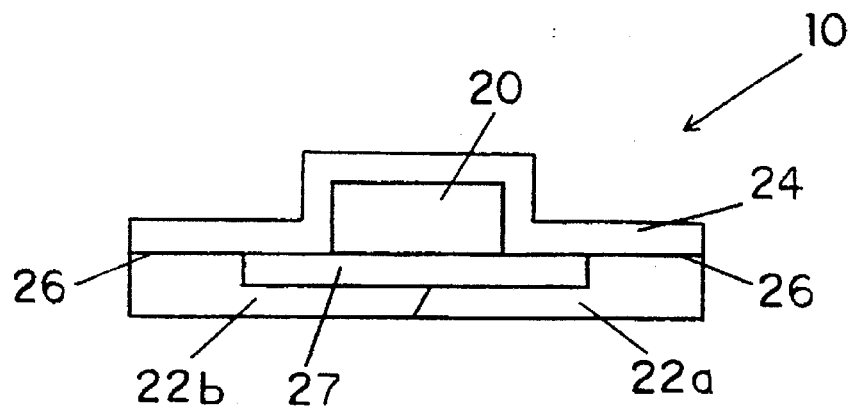
FIG. 1 is a cut-a-way side view of an on-site delivery system for low viscosity liquids incorporating a dimensionally stable reservoir.

FIG. 1 illustrates an on-site delivery system (10) comprised of dimensionally stable reservoir (20) and transfer pad (27) covered by securing protective sheet (24) with adhesive underside (26) and removable protective covers (22a–b). Reservoir (20) is composed of nonreactive materials such as sintered glass, sintered metals, ceramics, porous ultrahigh molecular weight polyethylene, polyvinylidene fluoride, polypropylene, and other materials which are capable of preventing the application liquid from draining out of reservoir (20) due to gravitational forces or compressive forces up to at least 1 psi. The preferred material being porous polyethylene. Securing protective sheet (24) may be comprised of water proof tape or other materials that have an adhesive underside (26). Transfer pad (27) is composed of non-woven cotton or polyester. The preferred embodiment being Veratec #140060 which is a non-woven polyester. To utilize on-site delivery system (10) of FIG. 1, removable protective covers (22a–b) are detached from adhesive underside (26) of securing protective sheet (24). Transfer pad (27) is placed directly over the treatment site and adhesive underside (26) of securing protective sheet (24) is attached to the skin surrounding the treatment site. Although not shown, if transfer pad (27) is larger than the treatment site, a treatment area mask which defines the treatment site is used. The treatment area mask is comprised of waterproof tape or other non-porous materials.

Figure 2:
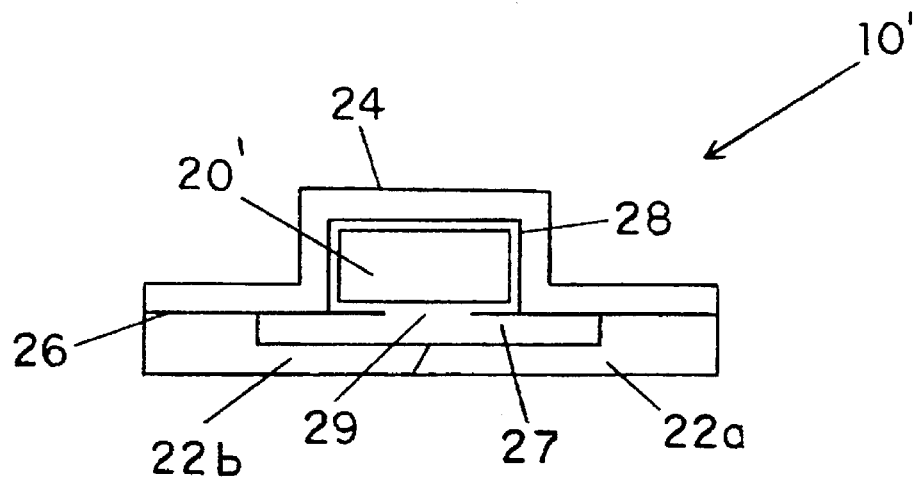
FIG. 2 is a cut-a-way side view of an on-site delivery system incorporating a reservoir surrounded by a dimensionally stable shell.

FIG. 2, illustrates an on-site delivery system (10') comprised of reservoir (20'), reservoir shell (28), transfer pad (27) securing protective sheet (24) with adhesive underside (26) and removable protective covers (22a–b). Reservoir (20') in FIG. 2 is not dimensionally stable and thus requires dimensionally stable reservoir shell (28). Reservoir (20') of FIG. 2 may be comprised of compressed polyester fibers or other absorbent materials. The preferred embodiment is polyester fiber. Reservoir shell (28) may be comprised of any material capable of withstanding at least 1 psi of pressure depending on the area to be treated. This is accomplished by using polyethylene, ceramics, or extruded shells comprised of various plastics or metals including aluminum. These materials also provide protection against ultraviolet and visible light and evaporation. The preferred embodiment is dependent on the treatment site. Reservoir shell (28) includes reservoir shell opening (29) which allows a portion of reservoir (20') to be in direct contact with transfer pad (27). To use on-site delivery system (10') of FIG. 2, removable protective covers (22a–b) are detached from adhesive underside (26) of securing protective sheet (24). Transfer pad (27) is placed directly over the treatment site and adhesive underside (26) of securing protective sheet (24) is attached directly to the skin surrounding the treatment site. The size of transfer pad (27) and reservoir shell opening (29) depends on the size of the treatment site. The larger the treatment site, the larger reservoir shell opening (29) is. Again, if transfer pad (27) is larger than the treatment site, a treatment area mask (not shown) is utilized.

Figure 4A:
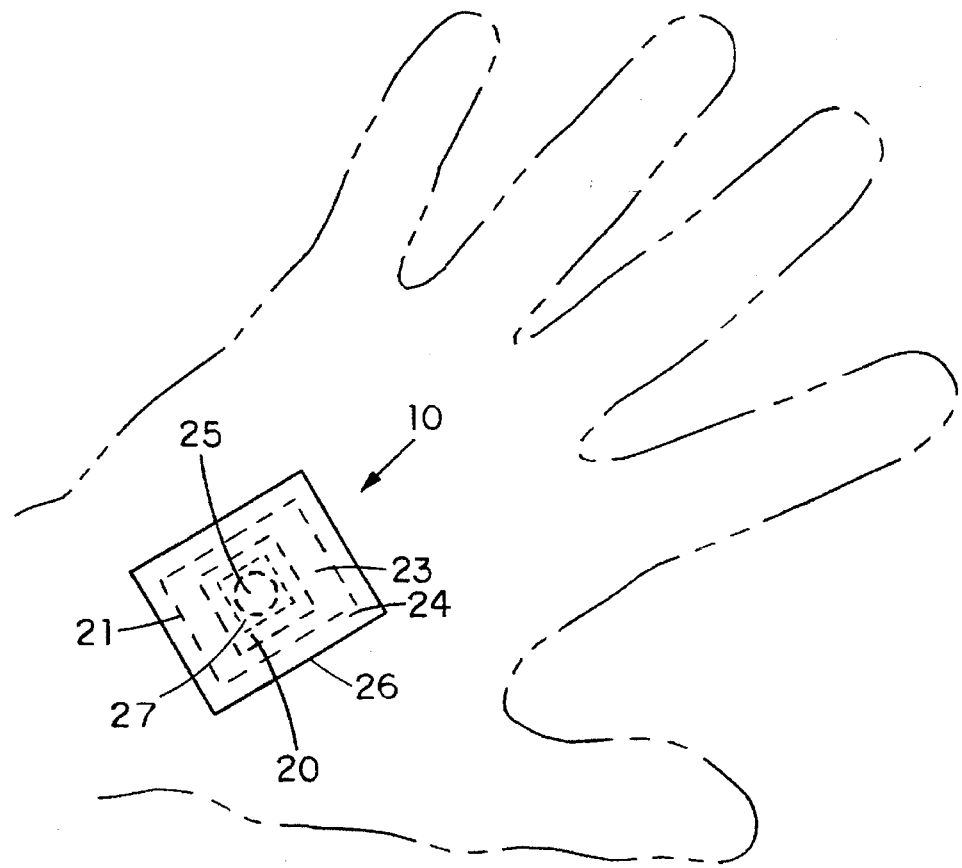
FIG. 4A is a top view of an alternative embodiment of an on-site delivery system with a dimensionally stable reservoir for use in conjunction with a treatment site smaller than the transfer pad.
Figure 4B:
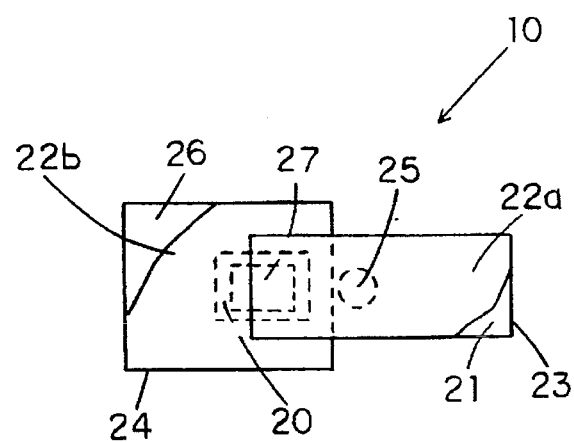
FIG. 4B is a cut-a-way top view of the alternative embodiment shown in FIG. 4A before it is attached to the hand.

FIG. 4A and 4B illustrate an embodiment of on-site delivery system (10) of FIG. 1 which incorporates a treatment area mask (23) with treatment site opening (25) and adhesive underside (21) for attaching treatment area mask (23) to the skin surrounding the treatment site. Treatment site opening (25) is sized dependent on the size of the treatment site. When not in use, adhesive underside (21) is attached to removable protective cover (22a) and securing protective sheet (24) with adhesive underside (26) attached to removable protective cover (22b). Reservoir (20) is attached to a portion of adhesive underside (26) of securing protective sheet (23). Transfer pad (27) is attached to reservoir (20). In FIGS. 4A and 4B, reservoir (20) is dimensionally stable although obvious changes to design could be made to incorporate a reservoir that is not dimensionally stable.

To use the embodiment shown in FIGS. 4A–B, removable protective cover (22a) is detached from adhesive underside (21) of treatment area mask (23). Treatment site opening (25) is placed over the treatment site with adhesive underside (21) of treatment area mask (23) attaching to the area surrounding the treatment site. Protective cover (22b) is detached from protective sheet (24). Transfer pad (27) and reservoir (20) are placed over treatment site opening (25) and protective sheet (24) is then attached to the skin via adhesive underside (26).

Figure 3:
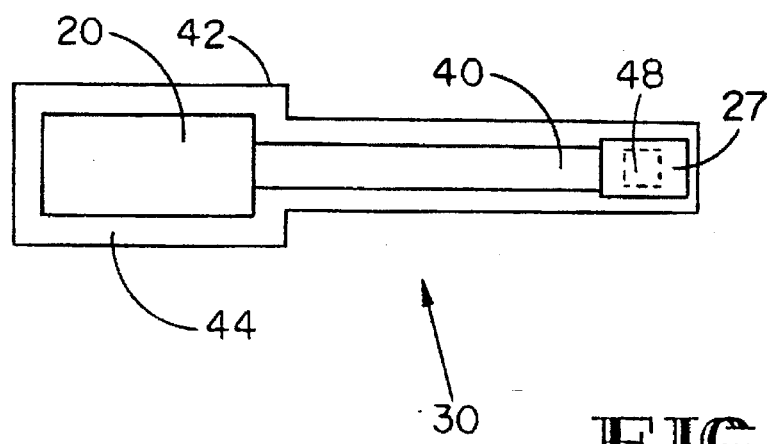
FIG. 3 is a cut-a-way top view of a remote-site delivery system which utilizes both a connector strip and a transfer pad.

FIG. 3 illustrates a remote-site delivery system (30) comprised of reservoir (20), connector strip (40), transfer pad (27) and system cover (42) with treatment site opening (48) and adhesive underside (44). System cover (42) encases the entire remote site delivery system (30). Connector strip (40) is comprised of woven polyester cloth or other materials capable of transferring liquid between reservoir (20) and transfer pad (27). If necessary, system cover (42) may be made of such materials that protect connector strip from compression as well as evaporation, ultraviolet and physical light. Reservoir (20) may be either dimensionally or non-dimensionally stable and composed of the materials previously discussed. Transfer pad (27) is also composed of the materials previously discussed. The design of remote-site delivery system (30) would of course change dependent on the composition of reservoir (20), transfer pad (27) and connector strip (40) because system cover (42) may not be required and could be replaced by any material with an adhesive underside to assure reservoir (20), connector strip (40) and transfer pad (27) do not move during application. In addition, the embodiment illustrated in FIG. 3 could be modified to eliminate transfer pad (27) and use connector strip (40) as a transfer pad.

Figure 5:
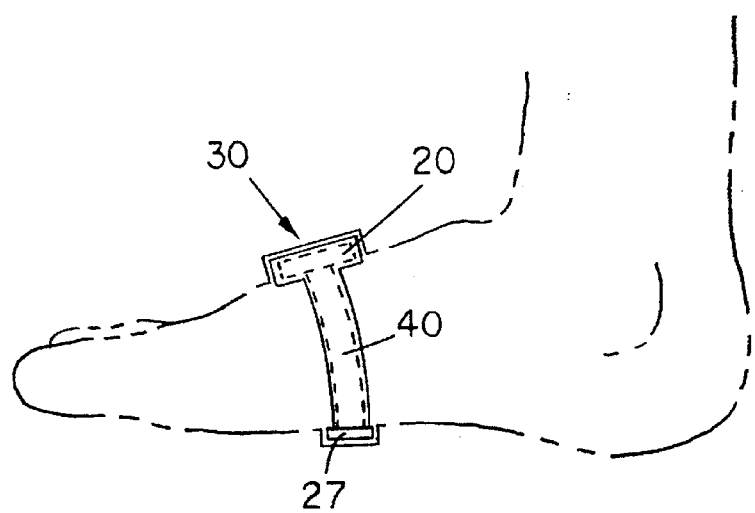
FIG. 5 is a side view of a remote-site delivery system attached to the top of a foot.
Figure 6:
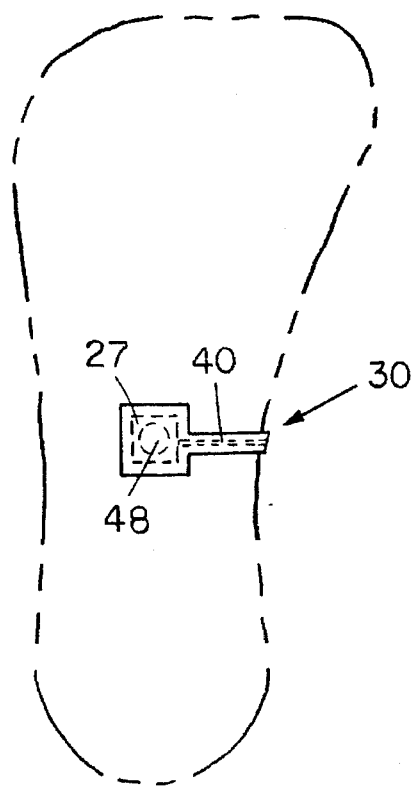
FIG. 6 is a top view of the underneath side of the foot in FIG. 5 to illustrate the attachment of the connector strip and transfer pad to the treatment site.

To use remote site delivery system (30) of FIG. 3, a removable protective cover (not shown) is detached from adhesive underside (44) of system cover (42). Treatment site opening (48) and transfer pad (27) is placed directly over the treatment site. Reservoir (20) is attached to the skin above the treatment site via adhesive underside (44) of protective system cover (42). Reservoir (20) is placed above transfer pad (27) to assure proper application. FIGS. 5 and 6 illustrate remote-site delivery system (30) of FIG. 3 in use as described.

Figure 7:
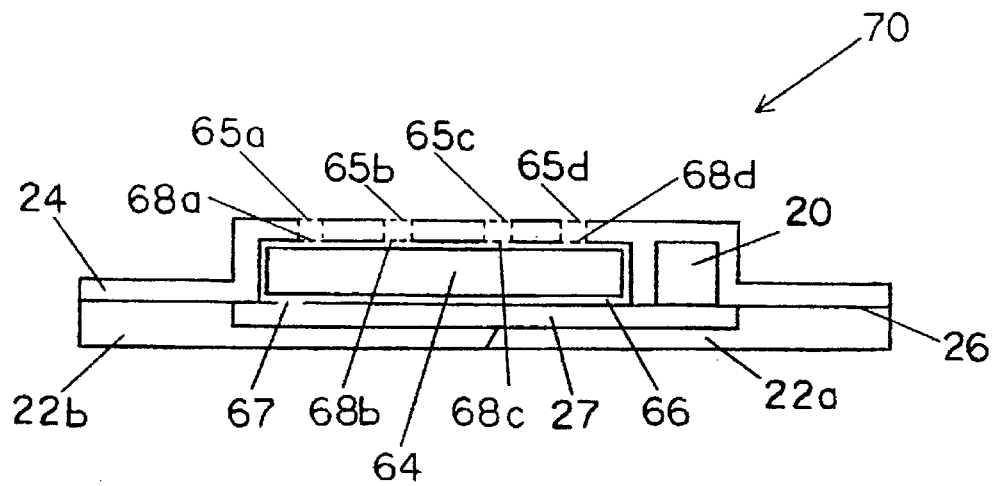
FIG. 7 is a cut-a-way view of the multi-action delivery system.

FIG. 7 illustrates a multi-action delivery system (70) comprised of reservoir (20), transfer pad (27), collection reservoir (64), protective cover (24) with adhesive underside (26), removable protective covers (22a–b) and vents (65a–d). Protective cover (24) is composed of waterproof tape or other materials that have an adhesive underside to assure multi-action delivery system (70) does not move during application. Collection reservoir (64) is comprised of a porous, extra absorbent material such as gauze or cotton and is encased in non-penetrable shell (66) with treatment site opening (67) and vents (68a–d). The high absorbency of collection reservoir (64) assures fluids will not return to the wound if multi-action delivery system (70) is left on after the application fluid has been delivered to the treatment site from reservoir (20). Non-penetrable shell (66) assures the application liquid will come in contact with the treatment site before being absorbed by collection reservoir (64) through treatment site opening (67) of collection reservoir (64).

EXAMPLE 1

A delivery system as illustrated in FIG. 2 with a separate treatment area mask was used to remove a wart. The reservoir was bonded nylon 3×5×15 mm in dimension covered with a polyethylene shell. The protective cover was Johnson & Johnson 1" waterproof tape. The transfer pad was a 5 mm×5 mm strip of Sontara® by Dupont. The treatment area mask was cut to expose only the wart and attached to the skin. The delivery system was then attached over the exposed skin. 0.180 mls of the following wart removal formula was injected into the reservoir.

| Ingredient | Percent by Weight |
| --- | --- |
| Salicylic acid | 20.13 |
| Propylene Glycol | 42.60 |
| Deionized Water | 10.65 |
| Anhydrous Alcohol | 26.62 |

After 6 hours, the delivery system was removed. The wart had a white appearance and completely sloughed off in 6 days without additional treatment.

EXAMPLE 2

5 mls of the formula of Example 1 was used in conjunction with a modified version of the FIG. 3 embodiment to treat rough hardened skin on the heel. In this particular example, the transfer pad was much larger than shown in FIG. 3 and the system cover did not encase the system. Consequently, a treatment site opening was not required. The transfer pad was a 6"×2" piece of DuPont Sontara® #8423 (rayon 70%, polyester 30%). The transfer pad was attached to a Transorb® polyester reservoir (American Filtrona) via a 3 inch polyethylene covered 6 mm wide strip of Sontara®. The entire assembly was secured with adhesive tape. After 4 hours, all of the skin in contact with the transfer pad was white in color. In 6 days the entire area of skin sloughed off revealing a layer of soft pink skin. No irritation or untoward effect was observed.

EXAMPLE 3

8 mls of the following formula was used in conjunction with a modified version of the FIG. 3 embodiment to treat a chronic case of athlete's foot. The transfer pad was a 12 cm×4 cm strip of Sontara®. The reservoir was a 1 mm×1 mm×5 mm strip of American Filtrona's nylon fiber block.

| Ingredient | Percent by Weight |
| --- | --- |
| Salicylic acid | 21.7 |
| Dimenethyl Isorbide | 34.8 |
| Anhydrous Alcohol | 43.5 |

The area between the toes was infected with fissures and red itchy skin. One 4 hour treatment was used. The intense itching stopped on contact. The entire stratum corneum sloughed off in 7 days, leaving healthy skin with no evidence of infection. Reexamination after 60 days revealed normal skin.

EXAMPLE 4

150 ul of 50% lactic acid was absorbed on a 10 mm×70 mm piece of Sontara® (Dupont) used as the connector strip as shown in FIG. 3. At the time of use, a 10 mm×15 mm×5 mm nylon reservoir (American Filtrona) was filled with water and placed in contact with the above connector strip. The water migrated from the reservoir through the connector strip and transferred the lactic acid quantitatively to a 3 mm×5 mm transfer pad of Sontara®. The transfer pad was totally wetted in about 10 minutes. This illustrates that all the ingredients of the treatment liquid need not be placed in the reservoir.

Although this Example illustrates impregnating the connector strip with a liquid, the connector strip could also be impregnated with a solid that is not stable in solution. The reservoir would then be filled with a solution capable of dissolving the solid impregnated in the connector strip and carrying it, in solution, to the transfer pad.

EXAMPLE 5

The FIG. 1 embodiment could be used to treat a lesion on the face. For example, 180 uls of 1 percent fluorouracil could be added to the reservoir. The reservoir could be a light density polyethylene by Porex Technologies. The transfer pad of polyester celulose (Veratec) would be cut to fit the size of the lesion. The FIG. 1 embodiment would be attached for 12 hours. Redness would appear in one day, followed by scaling and healing in one week.

EXAMPLE 6

The embodiment of FIG. 7 could be used to bathe a wound to enhance healing time. For example, the reservoir could be filled with 10 ml of antibiotics which would continuously bathe the wound to enhance healing time. The reservoir could be a medium density polyethylene by Porex Technologies, the transfer pad could be made of polypropylene, and the collection reservoir could be a medium density polyethylene product.

EXAMPLE 7

The embodiment of FIG. 1 could be used to treat age spots. For example, 100 ul of 4 percent hydroquinone, a depigmenting solution, would be added to the reservoir. The transfer pad would be cut to fit the size of the age spot. The reservoir could be a polyethylene product by Porex Technologies, and the transfer pad could be a polyester/cellulose product by Veratec. The FIG. 1 embodiment would be attached to the skin at the age spot daily for four hours until the age spot disappeared.

EXAMPLE 8

Insect bites could also be treated using the embodiment of FIG. 1. A sufficient quantity of the following material could be placed into the reservoir. The transfer pad would be placed directly over the insect bite for treatment.

| Ingredient | Percent by Weight |
| --- | --- |
| Benzocaine | 4.0 |
| Propylene glycol | 20.0 |
| Deionized Water | 76.0 |

The reservoir could be HPDE (Porex product with a 45% pore volume), 6 mm diameter by 1 mm thick, and the transfer pad could be a Veratec product classified as #1308221 which is a polyester/cotton material.

I claim:

1. A delivery system for applying liquids having a viscosity less than 1000 cPs to a treatment site without the migration of said liquids outside of said treatment site, comprising:

a reservoir having an upper side and an underneath side for placement of said liquids, said reservoir comprised of a dimensionally stable material which prevents said liquids from draining from said reservoir due to gravitational forces or compressive forces of 1 psi or less, wherein said dimensionally stable material is selected from the group consisting of sintered glass, sintered metals, ceramics, porous polyvinylidene fluoride polymer, porous polypropylene polymer, and bonded nylon fibers;

an absorbent transfer pad having an upper side and an underneath side, a portion of said upper side of said transfer pad contacting said underneath side of said reservoir and a portion of said underneath side of said transfer pad contacting said treatment site; and an attaching means for maintaining said delivery system in a position wherein said portion of said underneath side of said transfer pad remains in contact with said treatment site.

2. The delivery system of claim 1 further comprising a nonporous mask, said nonporous mask framing said treatment site and having an adhesive underside which attaches to the skin surrounding said treatment site and having an opening which allows said transfer pad to contact said treatment site.

3. The delivery system of claim 1 wherein said transfer pad is an inert, soft, flexible material for providing contact with said treatment site.

4. A delivery system for applying liquids having a viscosity less than 1000 cPs to a treatment site without the migration of said liquids outside of said treatment site, comprising:

a reservoir having an upper side and an underneath side for placement of said liquids, said reservoir comprised of a dimensionally stable material which prevents said liquids from draining from said reservoir due to gravitational forces or compressive forces of 1 psi or less, wherein said dimensionally stable material is selected from the group consisting of sintered glass, sintered metals, ceramics, polyvinylidene fluoride polymers, polypropylene polymers, bonded nylon fibers, or bonded polyester fibers;

an absorbent transfer pad having an upper side and an underneath side, a portion of said upper side of said transfer pad contacting said underneath side of said reservoir and a portion of said underneath side of said transfer pad contacting said treatment site; and a connector strip having a first end and a second end, said first end of said connector strip contacting said underneath side of said reservoir, said second end of said connector strip contacting said upper side of said transfer pad;

said connector strip being surrounded by a nonabsorbent material with properly positioned openings to allow contact between said connector strip and said reservoir and between said connector strip and said transfer pad; and an attaching means for maintaining said delivery system in a position wherein said transfer pad contacts said treatment site and said reservoir is in a position above said transfer pad.

5. The delivery system of claim 4 further comprising a nonporous mask framing said treatment site and having an adhesive underside which attaches to the skin surrounding said treatment site and having an opening that allows said transfer pad to contact said treatment site.

6. The delivery system of claim 4, wherein said transfer pad is an inert, soft, flexible material for providing contact with said treatment site.

7. A delivery system for applying liquids having a viscosity less than 1000 cPs to a treatment site without the migration of said liquids outside of said treatment site, comprising:

a reservoir having an upper side and an underneath side for placement of said liquids, said reservoir comprised of a non-dimensionally stable material and surrounded by an inert, dimensionally stable shell capable of withstanding 1 psi or less of compressive force, said non-dimensionally stable material is cotton gauze, fiberglass, or materials made of polyester or cotton fibers and said dimensionally stable shell is ceramic, aluminum, steel, glass, polyethylene, polypropylene, nylon, barex, styrene, or polyvinyl chloride polymers, said dimensionally stable shell having an opening to allow contact between said reservoir and said transfer pad;

an absorbent transfer pad having an upper side and an underneath side, a portion of said upper side of said transfer pad contacting said underneath side of said reservoir and a portion of said underneath side of said transfer pad contacting said treatment site; and an attaching means for maintaining said delivery system in a position wherein said portion of said underneath side of said transfer pad remains in contact with said treatment site.

8. A delivery system for applying liquids having a viscosity less than 1000 cPs to a treatment site without the migration of said liquids outside of said treatment site, comprising:

a reservoir having an upper side and an underneath side for placement of said liquids, said reservoir comprised of a non-dimensionally stable material surrounded by a dimensionally stable shell capable of withstanding 1 psi or less of compressive force, said non-dimensionally stable material is cotton gauze, fiberglass, or polyester or cotton fibers and said dimensionally stable shell is ceramic, aluminum, steel, glass, polyethylene, polypropylene, nylon, barex, styrene, or polyvinyl chloride polymers, said dimensionally stable shell having an opening to allow contact between said reservoir and said connecting strip;

an absorbent transfer pad having an upper side and an underneath side, a portion of said upper side of said transfer pad contacting said underneath side of said reservoir and a portion of said underneath side of said transfer pad contacting said treatment site;

a connector strip having a first end and a second end, said first end of said connector strip contacting said underneath side of said reservoir, said second end of said connector strip contacting said upper side of said transfer pad;

said connector strip being surrounded by a nonabsorbent material with properly positioned openings to allow contact between said connector strip and said reservoir and between said connector strip and said transfer pad; and an attaching means for maintaining said delivery system in a position wherein said transfer pad contacts said treatment site and said reservoir is in a position above said transfer pad.

* * * * *